United States Patent
Bono

(12) 
(10) Patent No.: US 6,302,883 B1
(45) Date of Patent: Oct. 16, 2001

(54) BONE PLATE-RATCHETING COMPRESSION APPARATUS

(75) Inventor: Frank S. Bono, Leesburg, IN (US)

(73) Assignee: DePuy Acromed, Inc., Raynham, MA (US)

( * ) Notice: Subject to any disclaimer, the term of this patent is extended or adjusted under 35 U.S.C. 154(b) by 0 days.

(21) Appl. No.: 09/177,683

(22) Filed: Oct. 22, 1998

(51) Int. Cl.$^7$ .................................................. A61B 17/56
(52) U.S. Cl. .............................. 606/69; 606/61; 606/70
(58) Field of Search .................................. 606/61, 70, 71, 606/69, 72, 73; 411/388, 389

(56) References Cited

U.S. PATENT DOCUMENTS

| | | |
|---|---|---|
| 3,942,405 | 3/1976 | Wagner . |
| 4,223,585 * | 9/1980 | Barth et al. .......................... 411/389 |
| 4,696,290 * | 9/1987 | Steffee ................................... 606/70 |
| 4,854,311 | 8/1989 | Steffee . |
| 5,085,660 | 2/1992 | Linn . |
| 5,234,431 * | 8/1993 | Keller ..................................... 606/70 |
| 5,261,910 | 11/1993 | Warden et al. . |
| 5,261,911 | 11/1993 | Carl . |
| 5,281,910 | 1/1994 | Emmoto et al. . |
| 5,290,288 * | 3/1994 | Vignaud et al. ........................ 606/61 |
| 5,324,290 | 6/1994 | Zdeblick et al. . |
| 5,344,421 | 9/1994 | Crook . |
| 5,395,371 | 3/1995 | Miller et al. . |
| 5,423,826 | 6/1995 | Coates et al. . |
| 5,486,176 | 1/1996 | Hildebrand et al. . |
| 5,498,262 | 3/1996 | Bryan . |
| 5,522,816 | 6/1996 | Dinello et al. . |
| 5,601,553 | 2/1997 | Trebing et al. . |
| 5,613,967 | 3/1997 | Engelhardt et al. . |
| 5,681,312 | 10/1997 | Yuan et al. . |

FOREIGN PATENT DOCUMENTS 0 530 585 A2 3/1993 (EP) .
2 692 772 12/1993 (FR) .

OTHER PUBLICATIONS

"Raising the Standard A Little Higher" brochure LIT–Z–P–SS94, copyright 1995 by Sofamor Danek USA (2 pages).
"University$^{AM}$ Plate Titanium Anterior System™ Ordering Information for Implants and Instruments" brochure, copyright 1994 AcroMed Corporation (6 pages).
C. Hopf, E. Eysel, and J. Dubousset, "Preliminary Report on a New Anterior Spinal Instrumentation", European Spine Journal (1995, 4:194–199).
"Alpha Plaques Cervicales" brochure, published by Stryker.RTM Implants, France, Prior May 1996 (2 pages).
"Cervical Spine Locking Plate, Original Instruments and Implants of the Association for the Study of Internal Fixation AO/ASIF" brochure, published by Synthes, Art No. 036,063, copyright by STRATEC Medical, printed in Switzerland, May 1996.
"Kaneda Anterior Spinal Instrumentation System" p. B–9 from catalog of AcroMed Corporation.

* cited by examiner

Primary Examiner—Michael Buiz
Assistant Examiner—Julian W. Woo
(74) Attorney, Agent, or Firm—Maginot Addison & Moore

(57) ABSTRACT

A bone plate apparatus of the present invention includes a plate having a slot extending between the superior and inferior surfaces of the plate, and a rim extending about the slot which includes an interrupted surface, a fastener including a shaft formed for extension into the bone, a collar coupled to the shaft having an interrupted surface which mates with the interrupted surface of the rim of the slot, and a head coupled to the collar for movement in the slot, and a nut forred to cooperate with the head of the fastener to couple the interrupted surfaces of the fastener and the rim together, thereby locking the head in a fixed position within the slot.

23 Claims, 3 Drawing Sheets

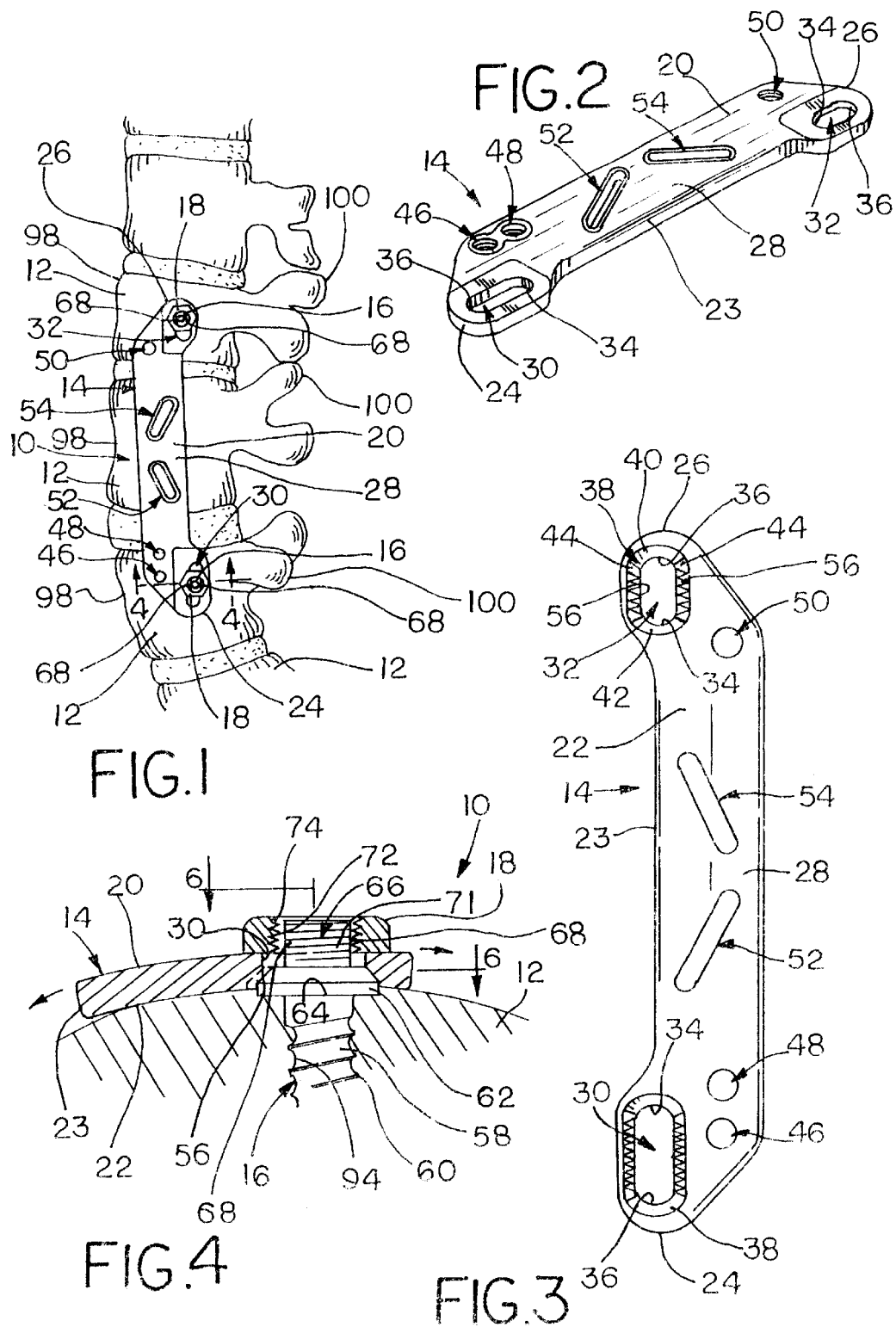

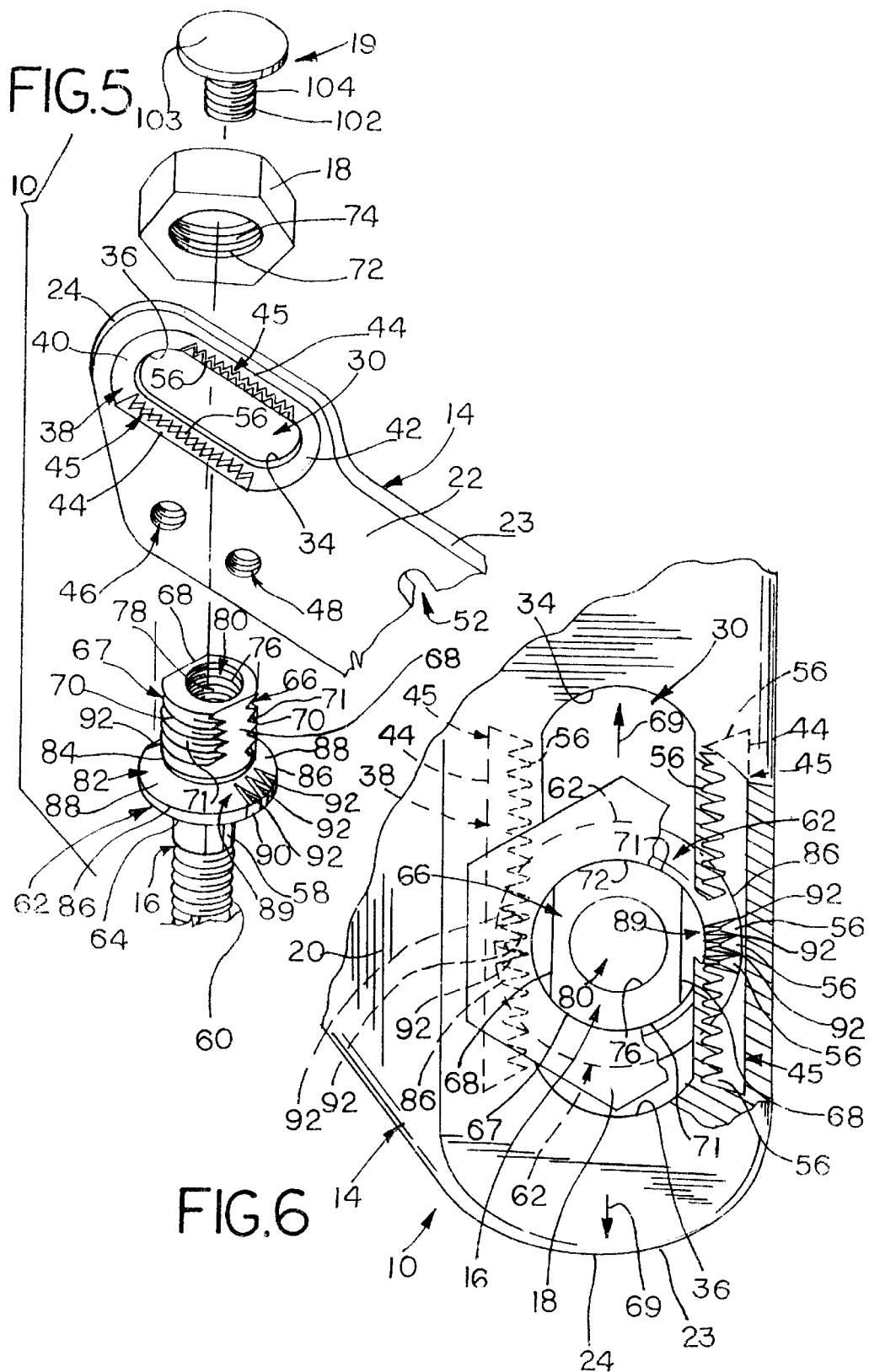

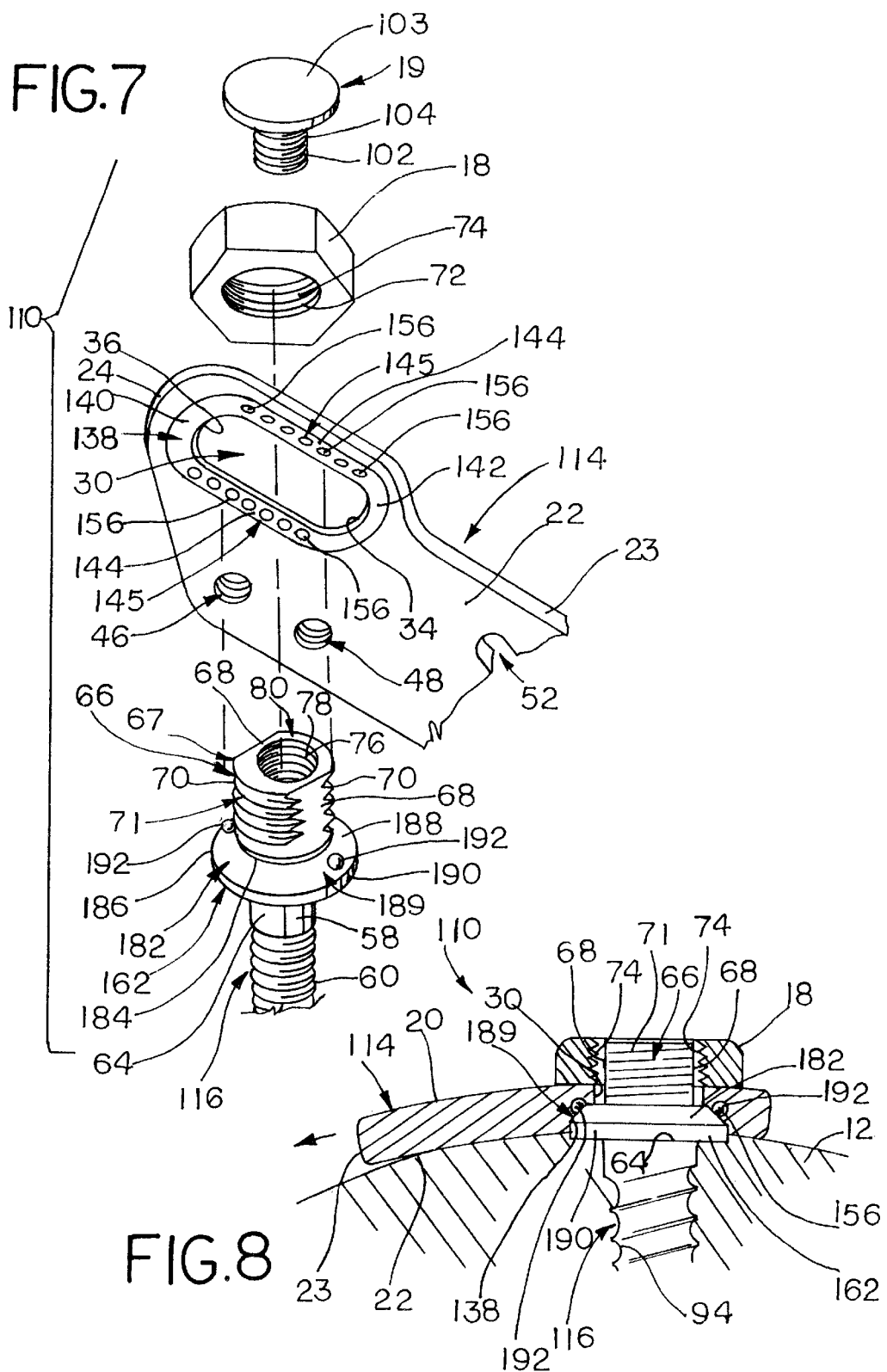

BONE PLATE-RATCHETING COMPRESSION APPARATUS

BACKGROUND AND SUMMARY OF THE INVENTION

The present invention relates to bone plates, more particularly the present invention relates to bone plates that apply compressive stress over a fracture. Most particularly, the present invention relates to bone plates that provide incremental compressive stress over a fracture.

Fasteners that thread into the vertebra are known, such fasteners, their structures and the manner in which they are used are taught in such prior art patents as U.S. Pat. No. 4,696,290 to Steffee; and U.S. Pat. No. 4,854,311 to Steffee; U.S. Pat. No. 5,613,967 to Engelhardt et al.; and U.S. Pat. No. 5,261,910 to Warden et al. and are incorporated herein by reference.

According to the present invention a bone plate apparatus is provided that preloads or provides incremental compressive stress over a fracture to aid in fusion. The plate apparatus includes a plate that is formed with spaced-apart slots and rims extending about the perimeter of each of the slots. The rim includes opposite interrupted surfaces extending along the lengths of the slots. In addition, the plate apparatus includes fasteners that are formed to be coupled to plate. Each fastener includes a shaft that extends into a vertebra, a collar coupled to shaft and formed to engage the plate, and a head that is sized for extension through the respective slot. The collar of the fastener includes an interrupted surface that is formed to mate with the interrupted surface of the rim of the plate. Nuts are also provided to cooperate with the heads of the fasteners to couple the interrupted surfaces of the fastener and rim together. Thus, the plate is prevented from moving relative to the vertebrae and the fasteners.

In preferred embodiments, the slots include a first end and a second end and the rims extend between the first and second ends. Each rim includes opposite ends adjacent to the first and second ends of the slots and side walls that extend between the opposite ends of the rim. The interrupted surface is formed on each of the side walls of the rim to mate with the interrupted surface formed on the collar of the fastener. The interruptions on the plate and fastener are preferably teeth that have a width of about 1 mm. In addition to spaced apart teeth providing the interruptions, it will be apparent that the interruptions made take the form of spaced apart bumps or indents that mate with corresponding spaced apart recesses. In this application and in the claims, therefore the term "interruptions" is intended to refer to spaced apart elements or recessed on the slots that mate or mesh with spaced apart elements or recesses on the fastener or locking device for fastener.

Therefore, according to the present invention a spinal plate assembly is provided that includes a plate having at least two elongated slots, a threaded fastener to extend through each slot into the spine, and a locking device to engage each fastener to hold it in a selected position in its slot. Each slot is formed with interruptions spaced along its length. In addition, cooperating interruptions are formed on the fastener or the locking device to mate with the slot's interruptions selectively to position the plate relative to the fastener.

Additional features of the invention will become apparent to those skilled in the art upon consideration of the following detailed description of preferred embodiments exemplifying the best mode of carrying out the invention as presently perceived.

BRIEF DESCRIPTION OF THE DRAWINGS

FIG. 1 is a perspective view of a bone plate apparatus as it would appear to a surgeon during attachment of the apparatus to a vertebrae of a patient, showing the apparatus including a bone plate formed to include spaced-apart slots and fasteners extending through the slots;

FIG. 2 is a perspective view of a bone plate of FIG. 1 showing the plate including a superior surface having opposite ends, the slots extending through the superior surface adjacent to the opposite ends, and elongated openings positioned to lie between the spaced-apart slots;

FIG. 3 is a bottom view of the bone plate of FIG. 2 showing an inferior surface of the plate and rims extending about each of the slots, the rims including teeth thereon;

FIG. 4 is a view taken along lines 4—4 of FIG. 1 showing the fastener including a threaded shaft extending into the vertebrae, a threaded head extending from the slot and coupled to a nut, and a collar positioned to lie between the shaft and the head and engaging the rim of the slot;

FIG. 5 is an exploded assembly view of the apparatus of FIG. 1 showing the collar including teeth that correspond with the teeth formed in the rim of the slot and showing an end screw that is formed for extension into a cavity formed in fastener once the surgeon has coupled the bone plate to the vertebrae;

FIG. 6 is a view taken along lines 6—6 of FIG. 4 showing the lock teeth of the collar engaging the teeth of the rim to hold the bold in a selected position on the bone plate;

FIG. 7 is an exploded assembly view of a bone plate apparatus in accordance with the present invention, showing the apparatus including a bone plate having an inferior surface formed to include a slot and a rim extending about the circumference of the slot and including apertures therein, a fastener including a threaded shaft, a threaded head, and a collar positioned to lie between the shaft and the head, the collar including protrusions thereon that correspond to the apertures formed on the rim, a nut formed to engage the threaded head of the fastener, and an end screw formed for extension through the nut and into a cavity formed in the head of the fastener; and FIG. 8 is a cross-sectional view of the apparatus of FIG. 7 showing the threaded shaft extending into the vertebrae, the threaded head extending from the slot and coupled to a nut, and protrusions on the collar engaging the apertures formed on the rim of the slot.

DETAILED DESCRIPTION OF THE DRAWINGS

As shown in FIG. 1, a bone plate apparatus 10 is provided in accordance with the present invention. Apparatus 10 preloads or provides incremental compressive stress in fine increments of at least about 1 mm over a fracture in a vertebra 12 to aid in fusion. It is appreciated that apparatus 10 preloads or provides incremental compression in fine increments over a graft in a vertebrectomy or corpectomy. Apparatus 10 includes a bone plate 14 configured to engage vertebrae 12, fasteners 16 extending through bone plate 14 into vertebrae 12, corresponding locking devices, such as nuts 18, and end screws 19 formed to engage fasteners 16.

Referring now to FIGS. 2 and 3, bone plate 14 includes a superior surface 20, an inferior surface 22, and an edge 23 extending between superior and inferior surfaces 20, 22. In addition, bone plate 14 includes opposite plate ends 24, 26 and a middle portion 28 positioned to lie between ends 24, 26. Slots 30, 32 are formed in bone plate 14 adjacent to ends 24, 26 respectively. Bone plate 14 further includes apertures 46, 48 positioned to lie adjacent to slot 30 and an aperture 50 positioned to lie adjacent to slot 32. Apertures 46, 48, 50 are sized to receive lock screws (not shown) once bone plate 14 has been coupled to vertebrae 12 by fasteners 16.

In addition, elongated openings 52, 54 are formed through bone plate 14 and are positioned to lie adjacent to middle portion 28 between slots 30, 32. Elongated openings 52, 54 are formed to receive a handle (not shown) that is used to move bone plate 14 from one location to another. It is appreciated may be formed to include any number of apertures in a variety of locations to receive a handle or other gripping apparatuses suitable for carrying bone plate 14 from one location to another.

As best shown in FIG. 3, slots 30, 32 are formed through bone plate 14 in general alignment with one another. Slots 30, 32 include a first end 34 and a second end 36 adjacent to respective ends 24, 26 of bone plate 14. Bone plate 14 further includes a tapered rim 38 extending about each slot 30, 32. While one rim 38 and slot 30 are illustrated and will be described hereafter it is understood that the description applies equally to both rims 38 and to slot 32. Rim 38 includes opposite ends 40, 42 adjacent to first and second ends 34, 36 of slot 30 and side walls 44 extending between ends 40, 42. Side walls 44 are each formed to include an interrupted surface 45. Surface 45 is interrupted by teeth 56 extending away from inferior surface 22. The width of teeth is about 1 mm. It is appreciated that the size and number of teeth may vary in accordance with the present disclosure. It is also appreciated that the rim may be formed on superior surface 20 without exceeding the scope of the present invention.

Fasteners 16 are sized for extension through slots 30, 32. One fastener 16 is shown in FIGS. 4–6, but it is appreciated that the following description applies to both fasteners. Fastener 16 includes a shaft 58 having threads 60, a collar 62 coupled to a superior end 64 of shaft 54, and a head 66 extending from collar 58. As shown in FIG. 5, head 66 is formed to include an exterior surface 67 that includes opposing sides 68 and opposite curved ends 71 that extend between sides 68. Sides 68 are generally flat and face side walls 44 of tapered rim 38 to permit head 66 to extend into slot 30 and slide between first and second ends 34, 36 of slot 30, as shown by arrows 69 in FIG. 6. Sides 68 are also formed to interact with side walls 44 of rim 38 to prevent fastener 16 rotating in slot 30 and backing out of slot 30. Ends 71 face first and second ends 34, 36 of slot 30 and include threads 70 that correspond with threads 72 formed on an interior surface 74 of nut 18. Head 66 also includes an interior surface 76 that includes threads 78 thereon and defines a cavity 80. Cavity 80 is sized to receive an end screw 19.

Collar 62 of fastener 16 includes a seat portion 82 that has a first end 84 adjacent to head 66, an opposite second end 86 spaced-apart from first end 84, and a center portion 88 positioned between ends 84, 86. Collar 62 also includes an edge 90 that extends from second end 86 of seat portion 82. See FIG. 5. Center portion 88 includes an interrupted surface 89 that is formed to mate with interrupted surface 45 of rim 28. Surface 89 is interrupted by teeth 92 that extend from center portion 88 between first and second ends 84, 86 to cooperate with teeth 56 of tapered rim 38 to lock fastener 16 in a fixed position within slot 30. Illustratively, three teeth 92 extend from center portion 88 of collar 62 adjacent to each side 68 of head 66. Each tooth 92 has a width of about 1 mm. It is appreciated that the size of teeth may vary and that greater or fewer than three teeth may be used in accordance with the disclosure to lock fastener 16 within slot 30. Thus, due to the interaction between teeth 56, 92, the number of fastener positions within slot 30 is limited by only the tooth 56, 92 width and the length of slot 30.

As shown in FIG. 5, end screw 19 is formed to include a shaft 102 sized for extension into cavity 80 of head 66 and an end cap 103 that engages nut 18. Shaft 102 is formed to include threads 104 that extend in a direction opposite than that of threads 70 of head 66. Therefore, if nut 18 should begin to rotate on head 66 in a nut disengagement direction away from bone plate 14, such rotation would serve to rotate end screw 19 in a screw engagement direction toward bone plate 14. Thus, end screws 19 act to block disengagement of nuts 18 from fasteners 16.

In use, the surgeon insets shaft 58 of each of the fasteners 16 into preformed apertures 94 in vertebrae 12 so that edge 90 of collar 62 engages an upper surface 96 of vertebrae 12. See FIG. 4. Referring now to FIG. 1, fasteners 16 are aligned in vertebrae 12 so that sides 68 are positioned to face anterior and posterior sides 98, 100 of vertebrae 12. Bone plate 14 is then placed upon upper surface 96 of vertebrae 12 so that heads 66 of fasteners 16 extend through respective slots 30, 32 and teeth 56 of rim 38 engage teeth 92 of collar 62. As shown in FIG. 5, when head 66 is placed through slot 30, sides 68 face side walls 44 of tapered rim 38. The surgeon is free to slide bone plate 14 relative to fasteners 16, such that fasteners 16 move between first end 34 and second end 36 of respective slots 30, 32.

Once the surgeon has selected a desirable position for bone plate 14 on fasteners 16, nuts 18 are threaded upon heads 66 of respective fasteners 16, as shown in FIG. 6. As nuts 18 are tightened on heads 66, teeth 56 of rim 38 are pressed between teeth 92 of collar 62. Once nuts 18 have locked teeth 56, 92 together, heads 66 of fasteners 16 are locked in a fixed position within slots 30, 32 and bone plate 14 is held in a fixed position on vertebrae 12. End screw 19 is then inserted into cavity 80 of head 66 and rotated until cap 103 engages nut 18.

Referring now to FIG. 7, a bone plate apparatus 110 is provided in accordance with the present invention. Apparatus 110 preloads or provides incremental compressive stress in fine increments over a fracture in a vertebra 12 to aid in fusion. Apparatus 110 includes a bone plate 114 configured to engage vertebrae 12, fasteners 116 extending through bone plate 114 into vertebrae 12, corresponding nuts 18, and end screws 19 formed to engage fasteners 116.

Bone plate 114 is formed in a manner similar to bone plate 14 and like reference numerals will be used to denote like components. Bone plate 114 includes a tapered rim 138 extending about slot 30 on inferior surface 22. Only one tapered rim 138 is shown in FIGS. 7 and 8, but it is appreciated that the following description applies to a rim that surrounds slot 32 in bone plate 114. Rim 138 includes opposite ends 140, 142 adjacent to first and second ends 34, 36 of slot 30 and side walls 144 extending between ends 140, 142. Side walls 144 each include an interrupted surface 145. Surface 145 is interrupted by a series of apertures 156.

Fastener 116 is sized for extension through slot 30. Fastener 116 is formed in a manner similar to fastener 16 and like reference numerals will be used to denote like components. One fastener 116 is shown in FIGS. 7 and 8, but it is appreciated that the following description applies to any number of fasteners suitable for use with bone plate 114. Fastener 116 includes a collar 162 coupled to superior end 64 of shaft 54. Head 66 extends from collar 162.

Collar 162 includes a seat portion 182 and an edge 190 that extends away from seat portion 182. As shown in FIG.

7, seat portion 182 has a first end 184 adjacent to head 66, an opposite second end 186 spaced-apart from first end 184 adjacent to edge 190, and a center portion 188 positioned between ends 184, 186. Center portion 188 of seat portion 182 includes an interrupted surface 189. Surface 189 is interrupted by protrusions 192 that extend from center portion 188 to cooperate with apertures 156 of tapered rim 138 to lock fastener 116 in a fixed position within slot 30. It is appreciated rim 138 could include protrusions and collar 162 could include apertures in accordance with the present disclosure. Illustratively, one protrusion 192 extends from center portion 188 of collar 162 adjacent to each wall 68 of head 66. It is appreciated that the size of protrusions 192 and apertures 156 may vary and that greater than one protrusion 192 may be used in accordance with the disclosure to lock fastener 116 within slot 30. Thus, due to the interaction between apertures and protrusions 156, 192, the number of fastener positions within slot 30 is limited by only the protrusion width and the length of slot 30.

In use, the surgeon insets shaft 58 of each fastener 116 into preformed apertures 94 in vertebrae 12 so that edge 190 of collar 162 engages an upper surface 96 of vertebrae 12. See FIG. 8. Similar to fasteners 16, fasteners 116 are aligned in vertebrae 12 so that walls 68 are positioned to face anterior and posterior sides 98, 100 of vertebrae 12. Done plate 114 is then placed upon upper surface 96 of vertebrae 12 so that heads 66 of fasteners 16 extend through respective slots 30, 32 and apertures of rim 138 receive protrusions 192 of collar 162. As shown in FIG. 8, when head 66 is placed through slot 30, walls 68 face side walls 144 of tapered rim 138. The surgeon is free to slide bone plate 114 relative to fasteners 116, such that fasteners 116 move between first end 34 and second end 36 of respective slots 30, 32.

Once the surgeon has selected a desirable position for bone plate 114 on fasteners 116, nuts 18 are threaded upon heads 66 of respective fasteners 116, as shown in FIG. 8. As nuts 18 are tightened on heads 66, protrusion 192 of collar 162 is pressed into one of the apertures 156 in rim 138. Once nuts 18 have locked protrusion 192 in aperture 156, heads 66 of fasteners 116 are locked in a fixed position within slots 30, 32 and bone plate 114 is held in a fixed position on vertebrae 12. End ;crew 19 is then inserted into cavity 80 of head 66 and rotated until cap 103 engages nut 18.

Interrupted surfaces of the present disclosure are not limited to the teeth and the protrusion and aperture illustrated in FIGS. 1–8. It is appreciated that the interruptions may be any number of detents, stops, tabs, and the like that serve to lock the fastener in a fixed position within the slot. According to the present invention, the interrupted surface of the fastener or locking device mates with the interrupted surface of the plate to lock the fastener in a fixed position within the slot. Thus, the number of fixed fastener positions within slot 30 is limited by only the width of the interruptions and the length of slot 30.

Although the invention has been described with reference to certain embodiments, variations exist within the scope and spirit of the invention as described and defined in the following claims.

What is claimed is:

1. A bone plate apparatus comprising:

a plate including a superior surface, an inferior surface adapted to face the bone to be repaired, a slot extending between the superior and inferior surfaces, and an interrupted surface formed on the inferior surface adjacent the slot, a fastener including a shaft formed for extension into the bone, a collar coupled to the shaft, and a head coupled to the collar for movement in the slot, the head including a cavity, the collar including an interrupted surface, the interrupted surface of the collar being formed to mate with the interrupted surface of the inferior surface, a nut formed to cooperate with the head of the fastener to couple the interrupted surfaces of the fastener and inferior surface together and lock the head in a fixed position within the slot, and a screw formed to cooperate with the cavity to block the nut from disengagement from the head.

2. The apparatus of claim 1, wherein interrupted surface of the inferior surface includes teeth.

3. The apparatus of claim 2, wherein the teeth each have a width of about 1 mm.

4. The apparatus of claim 2, wherein the interrupted surface of the collar includes teeth.

5. The apparatus of claim 4, wherein the teeth have a width of about 1 mm.

6. The apparatus of claim 1, wherein the interrupted surface of the inferior surface includes apertures formed therein.

7. The apparatus of claim 1, wherein a rim is formed in the inferior surface of the plate, the rim including the interrupted surface of the inferior surface.

8. The apparatus of claim 7, wherein the rim includes opposite ends and side walls extending between the ends and the interrupted surface is formed on each of the side walls.

9. The apparatus of claim 8, wherein the head includes generally flat walls facing the side walls of the rim.

10. A bone plate apparatus comprising:

a plate including a superior surface, an inferior surface, and spaced-apart slots extending between the superior and inferior surfaces, the slots including a first end, a second end, and rims, the rims including opposite ends adjacent to the first and second ends of the slots and sidewalls extending between the opposite ends, the side walls each including an interrupted surface, fasteners including a shaft formed for extension into the bone, a collar coupled to the shaft, and a head coupled to the collar and sized for movement in the slot, the collar including an interrupted surface being formed to mate with the interrupted surface of the rim of the slot, and nuts formed to cooperate with the heads of the fasteners to couple the interrupted surfaces of the fastener and rim together and lock the head in a fixed position within the slot.

11. The apparatus of claim 10, wherein the head of the fastener is formed to include generally flat walls facing the opposite side walls of the rim.

12. The apparatus of claim 11, wherein the head of each fastener includes curved walls extending between the generally flat walls and the curved walls are formed to include threads that cooperate with each nut.

13. The apparatus of claim 10, wherein interrupted surface of the rim includes teeth.

14. The apparatus of claim 13, wherein the teeth have a width of about 1 mm.

15. The apparatus of claim 13, wherein the interrupted surface of the collar includes teeth.

16. A bone plate apparatus comprising:

a plate including a superior surface, an inferior surface and spaced-apart slots extending between the superior and inferior surfaces, each of the slots including a first end and second end, the inferior surface including rims extending about the respective slots, the rims including side walls extending between the first and second ends of the slots, the side walls each including an interrupted surface, fasteners including a shaft formed for extension into the bore, a collar coupled to the shaft and having a tapered surface formed to include interruptions thereon that mate with the interrupted surface of the rim of the slot, and a head coupled to the collar for movement in the respective slot, the head including generally flat walls extending from the collar in general alignment with the interruptions on the tapered surface and threaded walls extending between the generally flat walls, and nuts formed to cooperate with the threaded walls to couple the interrupted surfaces of the fasteners and rims together and lock the heads in a fixed position within the respective slot.

17. The apparatus of claim 16, wherein the interrupted surface of the rim includes teeth.

18. The apparatus of claim 17, wherein the interruptions on the tapered surface are teeth.

19. The apparatus of claim 18, wherein the teeth of the rim and the collar each have a width of about 1 mm.

20. The apparatus of claim 16, wherein the interruptions on the tapered surface have a width of about 1 mm.

21. A spinal plate assembly comprising:

a plate having at least two elongated slots, a threaded fastener to extend through each slot into the spine, a first locking device to engage each fastener to hold it in a selected position in its slot, and a second locking device to engage the threaded fastener to maintain engagement of the first locking device on the threaded fastener, the plate having a first interrupted surface on a side of the plate configured for facing the spine, the first interrupted surface being formed adjacent each slot, a second interrupted surface formed on the fastener to mate with the first interrupted surface to position the plate relative to the fastener.

22. The assembly of claim 21, wherein the fastener includes a collar and the second interrupted surface includes teeth formed on the collar.

23. The assembly of claim 22, wherein the first interrupted surface includes teeth.

* * * * *